United States Patent [19]
Leclercq et al.

[11] Patent Number: 6,069,294
[45] Date of Patent: May 30, 2000

[54] METHOD FOR CONTINUOUSLY PRODUCING SANITARY ARTICLES AND SANITARY ARTICLE PRODUCED

[75] Inventors: Maurice Pierre Leclercq, Abbeville; Jacques Dussaud, La Madeleine, both of France

[73] Assignee: Peadouce, Linselles, France

[21] Appl. No.: 08/321,159

[22] Filed: Oct. 11, 1994

Related U.S. Application Data

[63] Continuation of application No. 07/946,414, filed as application No. PCT/FR91/00341, Dec. 10, 1992, abandoned.

[30] Foreign Application Priority Data

May 7, 1990 [FR] France ..................... 90 05732

[51] Int. Cl.$^7$ ..................... A61F 13/15
[52] U.S. Cl. ............. 604/366; 604/385.2; 604/389; 156/66; 156/100; 156/163; 156/164; 156/279; 156/289
[58] Field of Search ............ 604/358, 365–366, 604/369–370, 372–373, 385.1, 385.2, 386, 389; 156/160–165, 176–179, 229, 289–291, 494–49, 537, 66; 428/40, 291, 352

[56] References Cited

U.S. PATENT DOCUMENTS

| | | | |
|---|---|---|---|
| Re. 31,922 | 6/1985 | Mesek et al. | 604/385.2 |
| 2,897,108 | 7/1959 | Harwood | 604/366 |
| 3,106,207 | 10/1963 | Dudley | 604/366 |
| 3,746,607 | 7/1973 | Harmon | 161/109 |
| 3,766,922 | 10/1973 | Krusko | 604/366 |
| 3,860,003 | 1/1975 | Buell | 604/385.2 |
| 3,985,136 | 10/1976 | Cepuritis | 604/398 |
| 4,045,833 | 9/1977 | Mesek et al. | 604/366 |
| 4,226,238 | 10/1980 | Bianco | 604/366 |
| 4,273,815 | 6/1981 | Gifford et al. | 428/35 |
| 4,351,784 | 9/1982 | Thomas et al. | 264/22 |
| 4,725,468 | 2/1988 | McIntyre | 604/385.2 |
| 4,731,066 | 3/1988 | Korpman | 604/366 |
| 4,771,483 | 9/1988 | Hooreman et al. | 2/237 |

FOREIGN PATENT DOCUMENTS

| | | |
|---|---|---|
| 0170922 | 2/1986 | European Pat. Off. . |
| 2588285 | 10/1986 | France . |
| SN 125480 | 1/1960 | New Zealand . |

*Primary Examiner*—John G. Weiss
*Assistant Examiner*—K. M. Reichle
*Attorney, Agent, or Firm*—Burns, Doane, Swecker & Mathis, L.L.P.

[57] ABSTRACT

A process for the continuous manufacture of articles of hygiene such as nappy-pants, of the type comprising an absorbent pad arranged between a liquid-impervious outer sheet and a liquid-permeable inner sheet, characterised in that absorbent pads are deposited at intervals onto a liquid-permeable continuous strip unwound from a reel in that a film of plastic material is extruded and deposited in the state where it has not yet solidified onto the strip and onto the pads, by applying the film against the strip and against the pads to make it adhere thereto and in that, after solidification of the film, a composite strip is cut transversely in the region situated between the absorbent pads, into individual articles.

5 Claims, 2 Drawing Sheets

METHOD FOR CONTINUOUSLY PRODUCING SANITARY ARTICLES AND SANITARY ARTICLE PRODUCED

This application is a continuation of Application Ser. No. 07/946,414, filed Dec. 10, 1992 and now abandoned, which is a 371 of PCT/FR91/00341.

FIELD OF THE INVENTION

The present invention relates to a process for the continuous manufacture of articles of hygiene such as nappy-pants, of the type comprising an absorbent pad arranged between a liquid-impervious outer sheet and a liquid-permeable inner sheet. The invention also relates to an article of hygiene thus manufactured.

BACKGROUND OF THE INVENTION

According to the usual processes for continuous manufacture of such articles, a continuous film of plastic, for example of polyethylene, is unwound from a reel and coated with lines or strips of adhesive of the hot melt type, individual absorbent pads which are at a distance from each other are deposited at intervals onto the film and then a continuous strip of permeable material, for example a strip of nonwoven, is applied onto the film and onto the pads so as to adhere to the said sheet at least along the lengthwise edges of the latter. When these articles are provided with lengthwise elastic members, continuous elastic members are coated with adhesive at least at intervals and are deposited in the stretched state onto the film before the application of the permeable strip onto the latter.

These known processes have a certain number of disadvantages.

Thus, the use of reels of polyethylene film imposes handling constraints and involves losses in time when the reels are changed. Bonding together the various constituent elements of the articles of hygiene (outer sheet, inner sheet, elastic and other members) involves a relatively high consumption of adhesive and imposes significant constraints (speed limitation, accuracy of application, etc).

Moreover, in the case of nappy-pants manufactured according to the usual processes, in the case of which the outer sheet adheres to the absorbent pads only along lines or strips at a distance from each other, the resistance and especially the tear resistance of the outer sheet of the nappy-pants is often inadequate to permit, after a first adhesive bonding, an unbonding of the adhesive fastenings with a view to their repositioning.

The subject of the present invention is a process for the continuous manufacture of articles of hygiene such as nappy-pants eliminating the constraints due to the use of polyethylene film in the form of reels to form the liquid-impervious outer sheet of the articles of hygiene and eliminating or at least considerably reducing the use of adhesive, for example of the hot-melt type to bond together the constituent elements of the articles of hygiene, as well as the constraints resulting from the use of adhesive. Another subject of the invention is a process for continuous manufacture of articles of hygiene enabling articles of hygiene of improved strength to be obtained.

A further subject of the invention is articles of hygiene such as nappy-pants manufactured at a reduced cost.

SUMMARY OF THE INVENTION

According to the process in accordance with the invention for the continuous manufacture of articles of hygiene such as nappy-pants, of the type comprising an absorbent pad arranged between a liquid-impervious outer sheet and a liquid-permeable inner sheet, individual absorbent pads are deposited at intervals onto a liquid-permeable continuous strip unwound from a reel. A film of plastic material is then extruded and deposited in the state where it has not yet solidified onto the said strip and onto the said pads, by applying the said film against the strip and against the pad, to make it adhere thereto. After solidification of the said film the composite structure is cut transversely into individual articles of hygiene in the region situated between the successive pads.

Since the extruded film is deposited and applied onto the strip and onto the pads before it solidifies, it adheres thereto without it being necessary to employ adhesive as according to known processes. In addition, the extruded film is bonded continuously, by direct bonding to the absorbent pads and to the strip over the whole area of contact and not only along the adhesive bonding lines at a distance from each other as according to the known processes. As a result, the cohesion and in particular the tear resistance of the outer sheet of the articles of hygiene is strengthened by the absorbent pad. It is thus possible to bond adhesively and to unbond the adhesive fastenings on this region of the outer sheet, with a view to repositioning the fastenings, even in the case where a relatively thin film is employed for the outer sheet.

For the continuous manufacture of articles of hygiene comprising lengthwise elastic members attached in the stretched state to the outer sheet, on both sides of the absorbent pad, it is proposed, according to the process in accordance with the invention, to deposit elastic members in the stretched state onto the said strip before the plastic film is extruded and deposited onto the strip and onto the pads, so that the said film also adheres to the said elastic members when it solidifies.

Consequently, the attachment of the elastic members also takes place without using adhesive.

According to known processes for the manufacture of nappy-pants comprising lengthwise elastic members which are attached to the impervious outer sheet only over a part of their length, namely in the crotch region of the nappy-pants, it is known to coat continuous elastic members with adhesive at intervals so that when the composite structure comprising an impervious strip, a permeable strip and absorbent pads at a distance from each other and arranged between the said two strips, is cut transversely, the elastic members contract freely in their parts which are not coated with adhesive. According to the process in accordance with the invention, arrangements are made, with a view to the manufacture of articles of hygiene comprising elastic members attached to the outer sheet only over a part of their length, to provide the continuous elastic members at intervals with a coating of antiadhesive material to prevent them from adhering in these regions to the film which is extruded and deposited in the state where it has not yet solidified onto the strip, the absorbent pads and the said continuous elastic members. Thus, when the composite structure is cut transversely into individual articles, these elastic members can contract freely in their parts provided with a coating of antiadhesive matter, since the film does not adhere to the elastic members in these parts.

According to another characteristic of the process in accordance with the invention, relating to the attachment of the adhesive fastenings for closing the nappy-pants, the adhesive fastenings are deposited and attached by adhesive bonding of their attachment parts onto the permeable strip before the film in the state where it has not yet solidified is deposited onto the said strip and the attachment parts of the adhesive fastenings. Thus, on the finished nappy-pants, the adhesive fastenings are firmly attached between, and adhere to, the permeable inner sheet, for example of nonwoven, and the impervious outer sheet, for example of polyethylene.

Furthermore, to manufacture nappy-pants comprising optionally elasticated transverse belt members, these transverse members are generally attached by adhesive bonding to the impervious outer sheet. According to the process in accordance with the invention, on the other hand, it is possible to attach these transverse belt members without employing adhesive, by depositing the said belt members onto the strip before extruding and depositing onto the strip the said film in the state which has not yet solidified. As a result, the transverse belt members are firmly attached without adhesive to this film and therefore to the impervious outer sheet on the nappy-pants.

BRIEF DESCRIPTION OF THE DRAWINGS

A more detailed description of the invention will be given below with reference to the attached diagrammatic drawings; on the drawings.

DETAILED DESCRIPTION OF THE PREFERRED EMBODIMENTS

Figure 1:
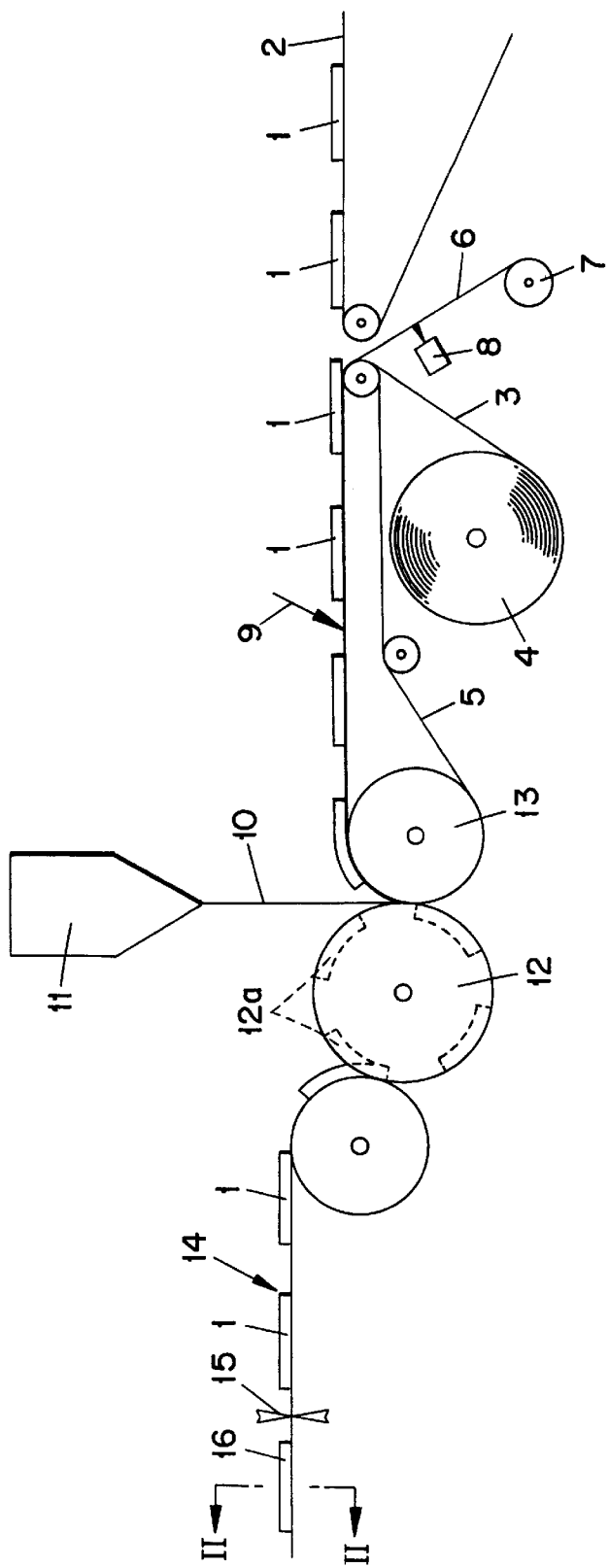
FIG. 1 shows a general outline of the process according to the invention for the manufacture of nappy-pants.

The process in accordance with the invention as illustrated in FIG. 1 consists in delivering absorbent pads 1, for example based on cellulose fluff, which are conveyed by a conveyor 2, onto a permeable strip 3, for example a strip of nonwoven, unwound from a reel 4, the strip 3 being supported by a conveyor 5, for example a suction conveyor belt. At the same time as the absorbent pads 1, continuous elastic members 6 drawn from a reel 7 are, after having been intermittently provided with a coating of antiadhesive matter, for example of silicone, at a coating station 8, deposited in the stretched state onto the strip 3, in the lengthwise direction of the latter, on both sides of the absorbent pads 1.

At the station 9, adhesive fastenings may be deposited onto the strip 5 so that their attachment parts overlap the lengthwise edges of the strip 3 in the vicinity of an end of each pad 1.

At the end of the conveying pathway defined by the conveyor belt 5, a film 10 of thermoplastic material, for example of polyethylene, extruded by a die 11, is deposited onto the strip 3 and onto all the other components (absorbent pads 1, elastic members 6, attachment parts of the adhesive fastenings) deposited previously onto the strip 3. The film 10, which may, for example, be between 5 and 30 μm in thickness, is applied in the state in which it has not yet solidified, against the strip 3 and the members carried by this strip, between a cooling roll 12 provided with cells 12a closely matching the shape of the pads 1 and a backing roll 13, also cooled and used at the same time as a return roll for the conveyor belt 5.

The width of the die 11 is preferably adjustable, and this makes it possible to extrude the film 10 in a width corresponding to the width of the articles of hygiene to be manufactured. After the film 10 has cooled, it adheres to one face of the absorbent pads 1 and all around the edges of the latter, whatever the shape of the pads (rectangular, hourglass-shaped), thus forming a leakproof barrier to liquids. In addition, the film 10 adheres to the strip 3 around the pads 1, over the whole surface of the strip 3 which is not covered by the pads 1.

The film 10 also adheres to the parts of the elastic members 6 which are not provided with a coating of antiadhesive matter. Finally, the film 10 adheres to the attachment parts of the adhesive fastenings deposited at 9 onto the strip 3.

After solidification of the film 10 on the roll 12, the composite structure 14 made up of the strip 3, the absorbent pads 1, the elastic members 6 and the adhesive fastenings is delivered to a transverse cutting station 15 at which the structure 14 is cut into individual articles of hygiene 16 in the region between each pair of successive absorbent pads 1.

Figure 3:
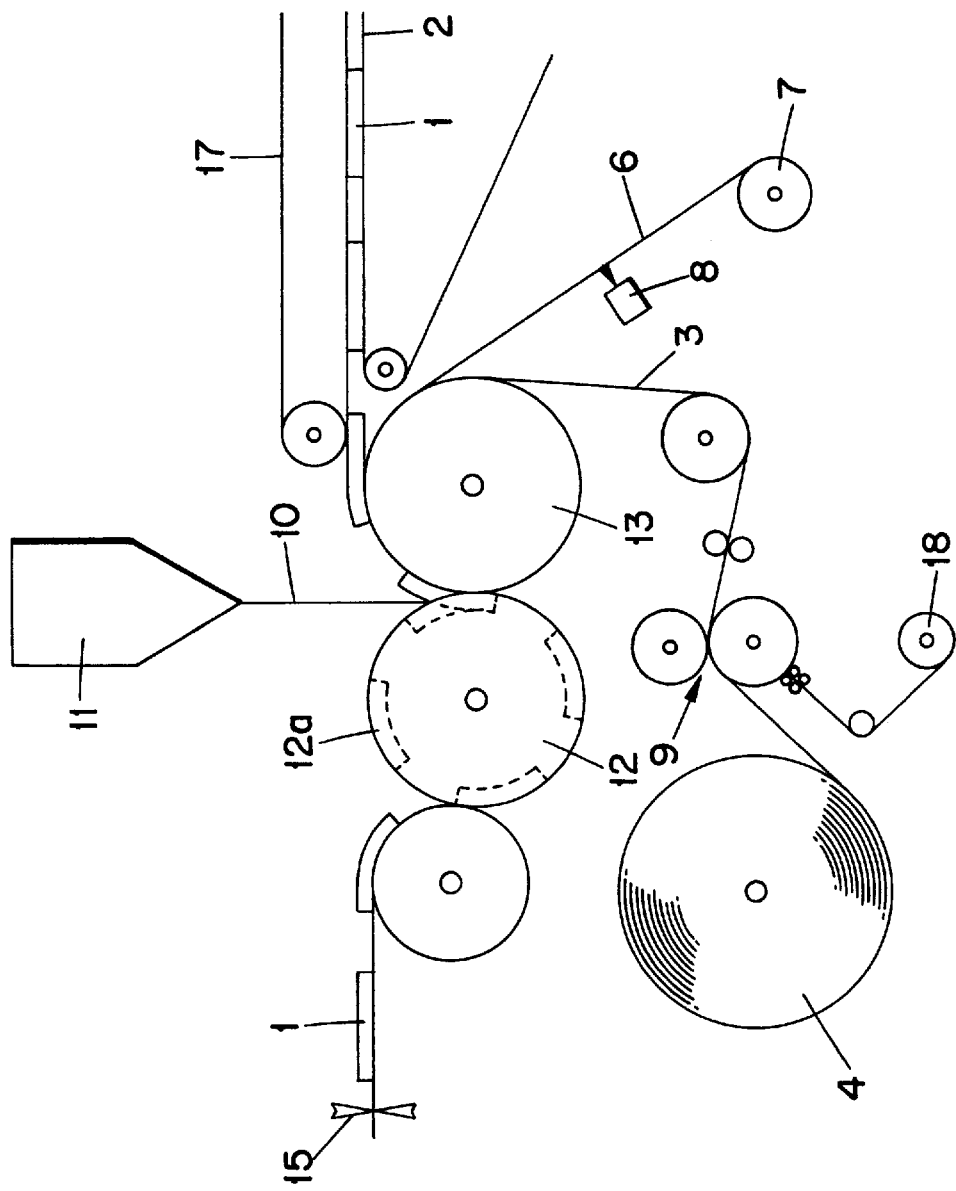
FIG. 3 shows a general layout of another embodiment of the process in accordance with the invention.

The process as illustrated by FIG. 3 differs from the process according to FIG. 1 in that the pads 1 delivered by the conveyor 2 while held by an upper strip 17, are delivered not onto a conveyor belt 5 but directly onto the backing roll 13 onto which there is also delivered from the reel 4 the strip 3 onto which the adhesive fastenings originating from a reel 18 have been adhesively bonded at 9 beforehand. The backing roll interacting with the cooling roll 12 which has cells 12a, comprises one or more suction segments which are not shown, which hold the pads in relation to the strip 3 until they come into contact with the film 10 extruded by the die 11.

It is obvious that the embodiments shown and described have been given merely by way of illustrative examples and that many modifications and alternative forms are possible within the scope of the invention.

Thus, placing of the adhesive fastenings, instead of being performed at the station 9 before the deposition of the film 10, could also take place after deposition of the film 10, the adhesive fastenings being then attached in the usual manner by adhesive bonding.

Furthermore, it would also be possible to deposit onto the permeable strip 3, before the deposition of the film 10, transverse belt members, optionally elastic and heat-shrinkable, so that the latter also adhere to the outer sheet (10) of the nappy-pants without employing adhesive. In the case of using elastic transverse belt members placed in the stretched state it would be necessary to provide a provisional adhesive bonding of these members, at least at their ends.

Instead of consisting of polyethylene which can be extruded at a temperature of the order of 300° C., the film 10 may consist of any other suitable thermoplastic material, for example EVA (ethylene/vinyl acetate copolymer) or EBA (ethylene/butyl acrylate copolymer), it being preferably possible for this film to be permeable to water vapour. This film, which may be coloured in bulk, may be of variable thickness (in the transverse direction and/or in the lengthwise direction) and may have elasticated regions, for example to form the belt region of the nappy-pants.

Similarly, the liquid-permeable strip 3 could consist of a permeable material other than nonwoven, for example a perforated sheet.

The absorbent pads 1, which may also be deposited onto the strip 3 in a number of parallel lines, which consequently makes it possible to increase the production capacity, may consist, for example, of cellulose fibres, fluff paste or any other material, for example hot-melt fibres which, by partial melting, enable the internal cohesion of the pad to be improved, or inorganic fibres or else a mixture of hot-melt fibres and/or of inorganic fibres with cellulose fibres. Furthermore, other constituents such as super absorbent materials in the form of particles or fibres may also be incorporated in the absorbent pads.

Figure 2:
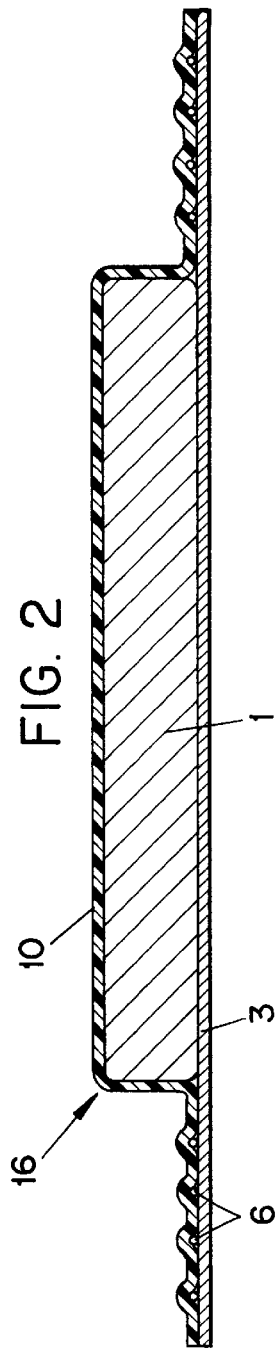
FIG. 2 is a cross-section along II—II of FIG. 1, on a larger scale, of a pair of nappy-pants produced according to the invention.

The elastic members 6 may be multi-strand members for example with four strands, as shown in FIG. 2, or also individual elastic members, with two strands and the like. To prevent the sheet 10 from adhering to the elastic members in the parts of the elastic members which are intended to contract after sectioning of the composite structure 14 at the cutting station 15, these elastic members may be provided with a coating of silicone or of any other suitable antiadhesive material.

Finally, the invention applies to the manufacture of articles of hygiene of all types (nappy-pants for children and adults, linings for the incontinent, sanitary towels) comprising an absorbent pad arranged between a liquid-impervious sheet and a liquid-permeable sheet, with or without elastic members.

We claim:

1. A process for the continuous manufacture of nappy-pants, each of the nappy-pants comprising an absorbent pad arranged between a liquid-impervious outer sheet made of a thermoplastic material and a liquid-permeable inner sheet made of a non-woven material, the process comprising:

depositing absorbent pads at intervals onto a liquid-permeable continuous strip made of a non-woven material unwound from a reel;

extruding a film of thermoplastic material;

depositing the film in the state where it has not yet solidified onto the strip and onto the pads, by applying the film against the strip and against the pads between a roll provided with cells closely matching the shape of the pads and a backing roll, wherein the pads are received in the cells and the film is made to adhere to one face of the absorbent pads and to the strip around the pads over the whole area of contact so as to form a composite strip; and after solidification of the the film, cutting the composite strip transversely between the absorbent pads.

2. The process of claim 1, for the manufacture of nappy-pants comprising lengthwise elastic members attached in the stretched state to the outer sheet on both sides of the absorbent pads, wherein continuous elastic members are deposited in the stretched state onto the said strip before the said film is extruded and deposited onto the strip so that said film also adheres to the said elastic members when it solidifies.

3. The process of claim 2, for the manufacture of nappy-pants in which the said elastic members are attached to the said sheet only over a part of their length, wherein the said continuous elastic members are provided at intervals with a coating of anti-adhesive material to prevent them from adhering in these regions to the film which is extruded and deposited in the state where it has not yet solidified onto the said strip, the said pads and the said elastic members.

4. The process of claim 2, for the manufacture of nappy-pants additionally comprising adhesive fastenings for closing the nappy-pants, wherein adhesive fastenings are deposited and attached by adhesive bonding onto the strip before the said film is extruded and deposited onto the strip so that the said film also adheres to the said fastenings when it solidifies.

5. The process of claim 2, for the manufacture of nappy-pants additionally comprising elasticated transverse belt members, wherein the said belt members are deposited onto the strip before the said film is extruded and deposited onto the strip so that the said film also adheres to the said belt members when it solidifies.

* * * * *